(12) United States Patent
Youker et al.

(10) Patent No.: US 7,646,614 B2
(45) Date of Patent: *Jan. 12, 2010

(54) THIN FILM DEPOSITION AS AN ACTIVE CONDUCTOR AND METHOD THEREFOR

(75) Inventors: Nick A. Youker, River Falls, WI (US); Ronald L. Anderson, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/123,261

(22) Filed: May 19, 2008

(65) Prior Publication Data

US 2008/0218989 A1  Sep. 11, 2008

Related U.S. Application Data

(60) Continuation of application No. 10/655,509, filed on Sep. 4, 2003, now Pat. No. 7,375,982, which is a division of application No. 09/499,725, filed on Feb. 8, 2000, now Pat. No. 6,631,555.

(51) Int. Cl.
  *H05K 9/00* (2006.01)
(52) U.S. Cl. .................. 361/816; 361/752; 174/258
(58) Field of Classification Search ............. 361/816, 361/800, 715, 752; 174/35 R, 51, 52.2, 76, 174/258; 257/665–666
See application file for complete search history.

(56) References Cited

U.S. PATENT DOCUMENTS

| | | | |
|---|---|---|---|
| 4,195,323 A | 3/1980 | Lee | |
| 4,616,655 A | 10/1986 | Weinberg et al. | |
| 5,012,190 A | 4/1991 | Dossel | |
| 5,120,578 A | 6/1992 | Chen et al. | |
| 5,236,510 A | 8/1993 | Brennesholtz | |
| 5,247,423 A | 9/1993 | Lin et al. | |
| 5,248,402 A | 9/1993 | Ballentine et al. | |

(Continued)

OTHER PUBLICATIONS

"U.S. Appl. No. 10/655,509, Notice of Allowance Mailed Jan. 3, 2008", 9 Pages.

(Continued)

*Primary Examiner*—Dean A. Reichard
*Assistant Examiner*—Yuriy Semenenko
(74) *Attorney, Agent, or Firm*—Schwegman, Lundberg & Woessner, P.A.

(57) ABSTRACT

A method includes populating components in a cavity of a substrate, disposing a polymer over the components and within the cavity. The polymer is cured and a thin film is formed on the polymer. In addition, a method includes forming an EMI shield within a medical device by depositing a thin film of metal on a surface within the medical device. The thin film of metal, of gold, aluminum, or copper, is formed by vapor deposition or sputtering. An apparatus includes a first substrate assembly including a first substrate having a cavity. A first set of electronic components are disposed within the cavity, and a first polymer is disposed over the first set of components. Deposited on an outer surface of the first polymer by vapor deposition is a thin film of metal. The thin film of metal is electrically coupled with a ground. A second substrate assembly including a second substrate is coupled with the first substrate assembly.

16 Claims, 6 Drawing Sheets

U.S. PATENT DOCUMENTS

| | | | |
|---|---|---|---|
| 5,280,192 A | | 1/1994 | Kryzaniwsky |
| 5,302,894 A | | 4/1994 | Hrubes |
| 5,376,825 A | | 12/1994 | Tukamoto et al. |
| 5,407,865 A | | 4/1995 | Glovatsky et al. |
| 5,470,345 A | | 11/1995 | Hassler et al. |
| 5,470,451 A | | 11/1995 | Kobayashi et al. |
| 5,552,633 A | * | 9/1996 | Sharma ..................... 257/700 |
| 5,594,204 A | | 1/1997 | Taylor et al. |
| 5,600,461 A | | 2/1997 | Ueda et al. |
| 5,650,593 A | | 7/1997 | McMillan et al. |
| 5,656,141 A | | 8/1997 | Betz et al. |
| 5,716,133 A | | 2/1998 | Hosokawa et al. |
| 5,736,856 A | | 4/1998 | Oliver et al. |
| 5,782,891 A | | 7/1998 | Hassler et al. |
| 5,796,165 A | | 8/1998 | Yoshikawa et al. |
| 5,814,090 A | * | 9/1998 | Latterell et al. ............... 607/36 |
| 5,856,915 A | | 1/1999 | Weinberg |
| 5,954,751 A | | 9/1999 | Chen et al. |
| 5,990,598 A | | 11/1999 | Sudol et al. |
| 5,994,898 A | | 11/1999 | DiMarzio et al. |
| 5,998,432 A | | 12/1999 | Walsh et al. |
| 6,011,993 A | | 1/2000 | Tzviskos et al. |
| 6,013,203 A | | 1/2000 | Paneccasio, Jr. et al. |
| 6,057,175 A | * | 5/2000 | Milla et al. ................. 438/113 |
| 6,101,100 A | | 8/2000 | Londa |
| 6,110,563 A | | 8/2000 | Pienimaa et al. |
| 6,156,641 A | | 12/2000 | Manning |
| 6,163,456 A | * | 12/2000 | Suzuki et al. ............... 361/704 |
| 6,245,092 B1 | * | 6/2001 | Schaldach, Jr. ................. 607/1 |
| 6,335,669 B1 | | 1/2002 | Miyazaki et al. |
| 7,375,982 B2 | * | 5/2008 | Youker et al. ............... 361/816 |

OTHER PUBLICATIONS

"U.S. Appl. No. 10/655,509 Response filed Sep. 20, 2007 to Final Office Action mailed Apr. 20, 2007", 10 Pages.

"U.S. Appl. No. 09/499,725 Advisory Action mailed Apr. 17, 2003", 3 pgs.

"U.S. Appl. No. 09/499,725 Final Office Action mailed Jan. 29, 2003", 10 pgs.

"U.S. Appl. No. 09/499,725 Non Final Office Action mailed Aug. 16, 2002", 11 pgs.

"U.S. Appl. No. 09/499,725 Notice of Allowance mailed May 14, 2003", 6 pgs.

"U.S. Appl. No. 09/499,725 Response filed Mar. 31, 2003 to Final Office Action mailed Jan. 29, 2003", 13 pgs.

"U.S. Appl. No. 09/499,725 Response filed Apr. 28, 2003 to Advisory Action mailed Apr. 17, 2003", 5 pgs.

"U.S. Appl. No. 09/499,725 Response filed Nov. 18, 2002 to Non Final Office Action mailed Aug. 16, 2002", 10 pgs.

* cited by examiner

THIN FILM DEPOSITION AS AN ACTIVE CONDUCTOR AND METHOD THEREFOR

CROSS-REFERENCE TO RELATED APPLICATION(S)

This application is a continuation of U.S. application Ser. No. 10/655,509, filed Sep. 4, 2003 now U.S. Pat. No. 7,375,982 which is a division of U.S. patent application Ser. No. 09/499,725, filed on Feb. 8, 2000, issued as U.S. Pat. No. 6,631,555, the specifications of which are incorporated herein by reference.

FIELD OF THE INVENTION

The present invention relates generally to electronics devices employing thin film deposition as an active conductor. More particularly, it pertains to medical devices such as an implantable pulse generator.

BACKGROUND OF THE INVENTION

Pulse generators such as pacemakers or defibrillators are implanted in the body for electrical cardioversion and/or pacing of the heart. Electrodes, which are used to apply electrical energy, are coupled with the pulse generator and are implanted in or about the heart. The electrodes are used to reverse (i.e., defibrillate or cardiovert) certain life threatening arrhythmias, or to stimulate contraction (pacing) of the heart. Electrodes have also been used to sense near the sinal node in the atrium of the heart and to deliver pacing pulses to the atrium.

A pulse generator is implanted during a surgical procedure under the skin of an individual. One desirable characteristic of such a device is that it has a relatively small volume or size. This is to increase the comfort to the patient, to prevent protrusion of the device from beneath the skin, and to prevent interference of the device with adjacent vital organs of the individual. One way to reduce the size of the pulse generator is to utilize small electronic components within the device, and to place the small electronic components closer together on the substrate. In addition, integrated circuit chip carriers are used to attach integrated circuits to circuit boards. The chip carriers allow for high density and complex interconnections between the integrated circuit and the circuit board.

When electronic components are placed closer together and/or complex interconnections are implemented, sensitive electronic circuitry and components are susceptible to electromagnetic interference (EMI) emanating from other circuits and components. One way to address the problem of EMI is to incorporate EMI shields to isolate the sensitive circuits from other circuits. The EMI shields are in the form of a separate piece of conductive tape or foil which is incorporated into the implantable device. The physical size of the foil limits efforts to reduce the overall size of the device, since the separate component consumes valuable space and volume within the implantable device.

In addition, electrical connections between the small electronic components must be made. Electrically conductive conduits are used to make electrical and mechanical connections between various circuits and discrete components in implantable defibrillators and pacemakers. One example of making such connections is metalized high temperature ceramic (HTCC) or metalized low temperature ceramic (LTCC). However, LTCC and HTCC technologies require screen printing specific traces on numerous specific ceramic layers followed by a high pressure lamination and elevated temperature (e.g. 850 degrees Celsius) to create a substrate of alternative conductors and insulators, which can be harmful to temperature sensitive components. Alternatively, printed circuit boards are another option. However, the printed circuit boards typically use etched copper foil which is laminated to a rigid organic fiber board in a multi layer arrangement using a variety of adhesive permanently binding the multi-layers together.

Accordingly, there is a need for reducing the overall size of the implantable device. There is also a need for an implantable medical device which simplifies the interconnect routing between the various electronic components of the device. Furthermore, there is a need to reduce EMI of the implantable medical device.

SUMMARY OF THE INVENTION

A method includes populating components in a cavity of a substrate, and disposing a polymer over the components within the cavity. The polymer is cured and a thin film of metal is formed on the polymer, where the polymer may have a non-planar surface on which the thin film of metal is deposited. The thin film of metal is vapor deposited on the polymer. Alternatively, the thin film of metal is sputtered on the polymer. The thin film of metal optionally includes a thin film of metal of the following materials: gold, aluminum, or copper. Optionally, the method includes electrically coupling the thin film of metal with an electrical ground. In another embodiment, the above assembly is coupled with a second substrate assembly, and the thin film is disposed between the two assemblies.

An alternative method includes forming an EMI shield within a medical device, where forming the EMI shield comprises depositing a thin film of metal on a surface within the medical device. In one embodiment, depositing the thin film of metal includes vapor depositing metal on the surface. Alternatively, depositing the thin film of metal includes sputtering metal on the surface. In another embodiment, the thin film is deposited on an insulator disposed within a case. The thin film of metal optionally includes a thin film of metal of the following materials: gold, aluminum, or copper. Optionally, the method includes electrically coupling the thin film of metal with an electrical ground. In another alternative, the EMI shield is formed by depositing the thin film of metal over insulation disposed over a resistor.

An apparatus is also provided herein where the apparatus includes a first substrate assembly including a first substrate having a cavity. A first set of electronic components are disposed within the cavity, and a first polymer is disposed over the first set of components. Deposited on an outer surface of the first polymer by vapor deposition is a thin film of metal. The thin film of metal electrically coupled with a ground. A second substrate assembly including a second substrate is coupled with the first substrate assembly. Optionally, the outer surface of the first polymer is non-planar. In another embodiment, the apparatus further includes a case having an insulator disposed therein. The first substrate assembly and the second substrate assembly are disposed between the insulator and the case, and a thin film of metal is vapor deposited on at least a portion of the insulator.

The method and structure described herein do not use or require any heat generation to deposit the thin film and/or conductive interconnects. In addition, the method can be used on a wide variety of materials while maintaining adequate adhesion and conduction sufficient for use in an implantable medical device such as a defibrillator or pacemaker. Further, the surface on which the traces are deposited is not limited in geometry or topography. Since the thin film does not require high temperature during the deposition or sputtering process, the components which populate the substrate will not be harmed by high temperatures. In addition, since the thin film layer can be deposited very thin, the size of the medical device is not unnecessarily increased.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
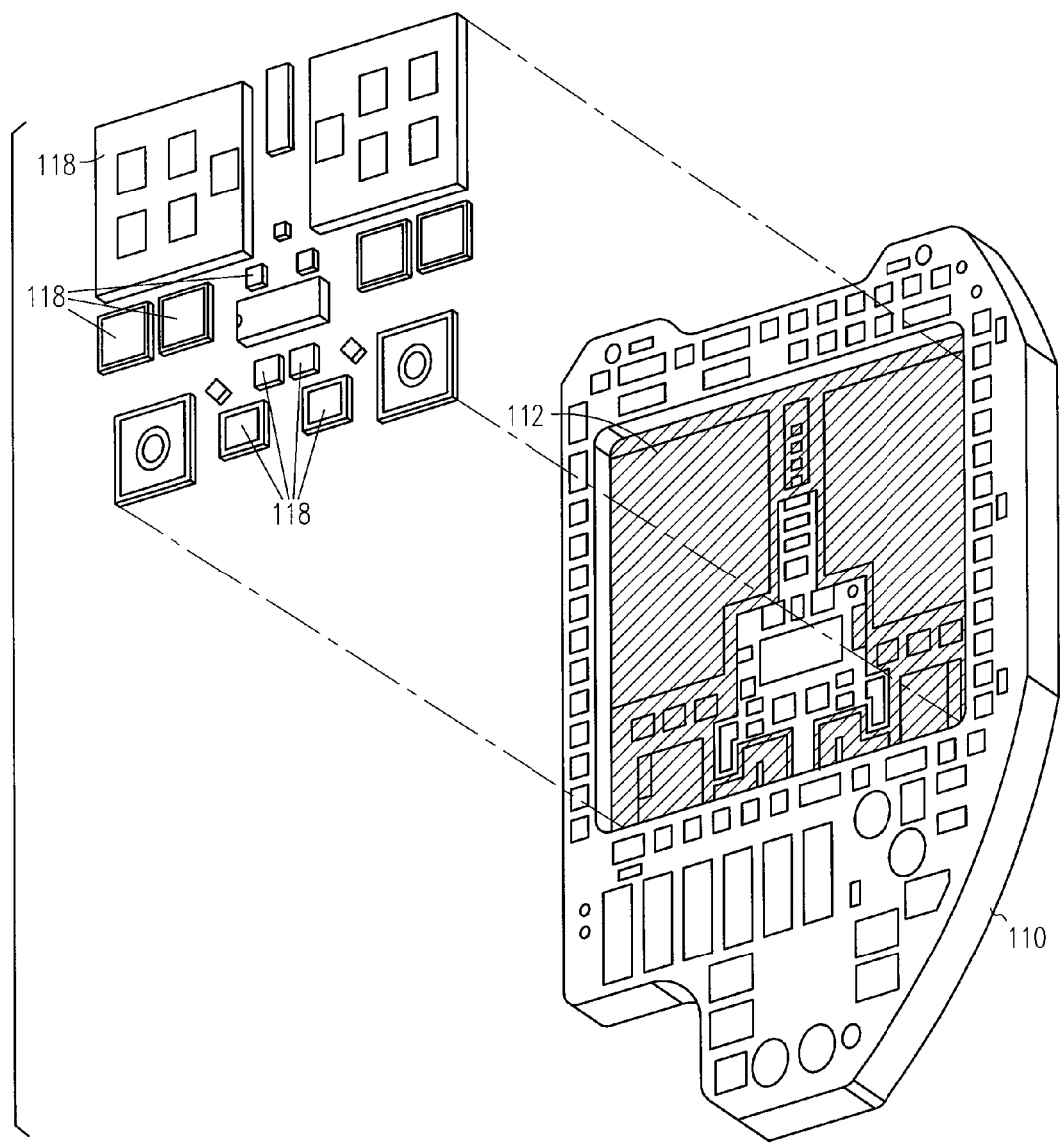
FIG. 1 is an exploded perspective view illustrating a substrate assembly constructed in accordance with one embodiment.
Figure 2A:
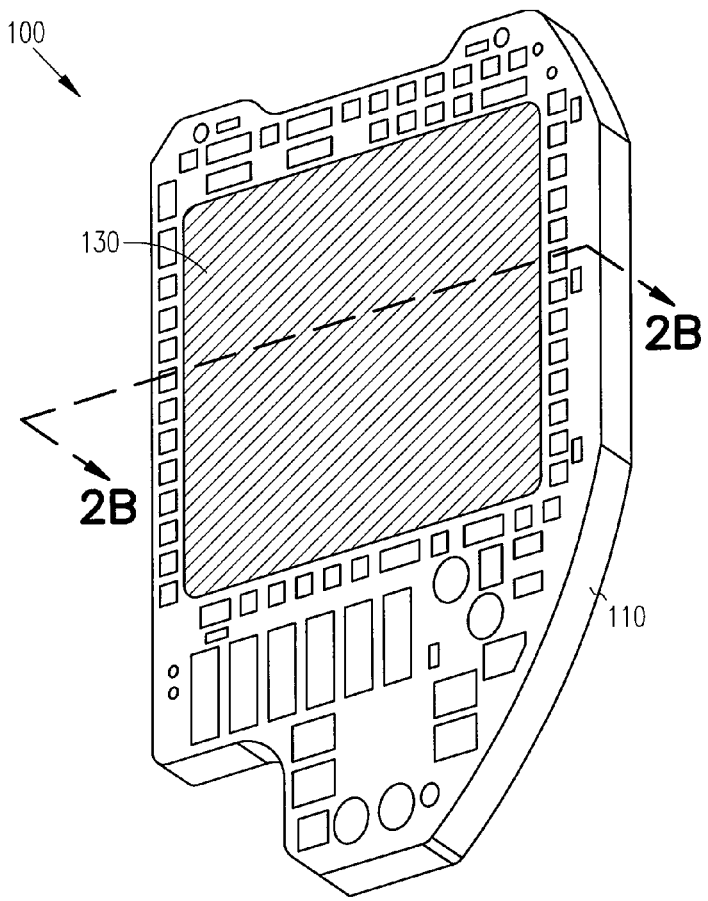
FIG. 2A is a perspective view illustrating an assembled substrate assembly constructed in accordance with one embodiment.
Figure 2B:
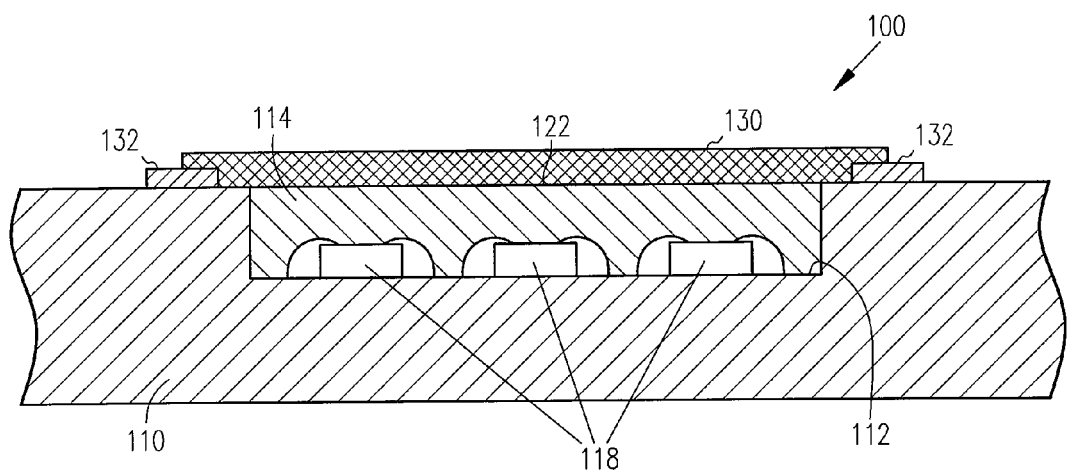
FIG. 2B is a cross-sectional view of FIG. 2A taken along 2B-2B.

FIGS. 1, 2A and 2B illustrate a substrate assembly 100 for use in a medical device, for instance, an implantable pulse generator. The substrate assembly 100 includes a substrate 110 having multiple components 118 disposed thereon. The substrate 110 has a cavity 112 therein, and the components 118 are populated on the substrate 110 within the cavity 112. The cavity 112 is filled with a dielectric polymer 114, where the polymer 114 is disposed over the components 118 to cover and insulate the components 118. In addition, the polymer 114 protects the components 118. One example of a suitable polymer is an epoxy. Other suitable materials include those which fill the voids or spaces amongst the components and which solidifies or becomes substantially rigid when cooled. The material should also have adequate compressive strength, and should also be lightweight. The polymer 114 assists in providing insulation between the components 118, and provides relatively high strength when it is cured. After the polymer 114 is disposed within the cavity 112, the polymer is cured at about 150 degrees C. to form a rigid to semi-rigid structure.

The polymer 114 is defined in part by an outer surface 122. A thin film metal is vapor deposited on the outer surface 122 of the polymer 114 to form a thin film 130, as shown in FIGS. 2A and 2B. To deposit the thin film metal, the atoms or molecules from a vaporization source reach the outer surface 122 of the polymer 114 without colliding with residual gas molecules. The vaporization source comprises one that thermally vaporizes materials, for example by evaporation or sublimation. Vacuum evaporation allows for a deposit of thin film of a variety of materials which can be deposited at high rates over large areas in a very pure form. The thin film 130 at least partially covers the outer surface 122, and optionally covers the entire outer surface 122 of the polymer 114. Alternatively, the thin film metal is sputtered on to the outer surface 122 to form a thin film 130. In contrast to the vapor deposition process which depends on heat to vaporize the material, sputtering is an atom-by-atom process. A target is bombarded by ions which physically chip atoms off of the target, causing them to be ejected from the target and subsequently strike the outer surface 122 and adhere thereto. The atoms build up on the second surface 122 to form a layer of material, resulting in the thin film 130. It should be noted that the thin film 130 can be formed on the outer surface 122 prior to the polymer 114 being fully cured, or can be formed on the outer surface 122 after the polymer 114 is fully cured. Further, the outer surface 122 is optionally non-planar. In one embodiment, the thin film 130 is formed to a thickness of about 25 microns. The thin film 130 is electrically coupled with a ground pin 132, as shown in FIG. 2B, such that the thin film 132 can be used for electrical isolation. The thin film 130 is formed from a variety of conductive materials including, but not limited to, gold, aluminum, or copper.

Figure 3:
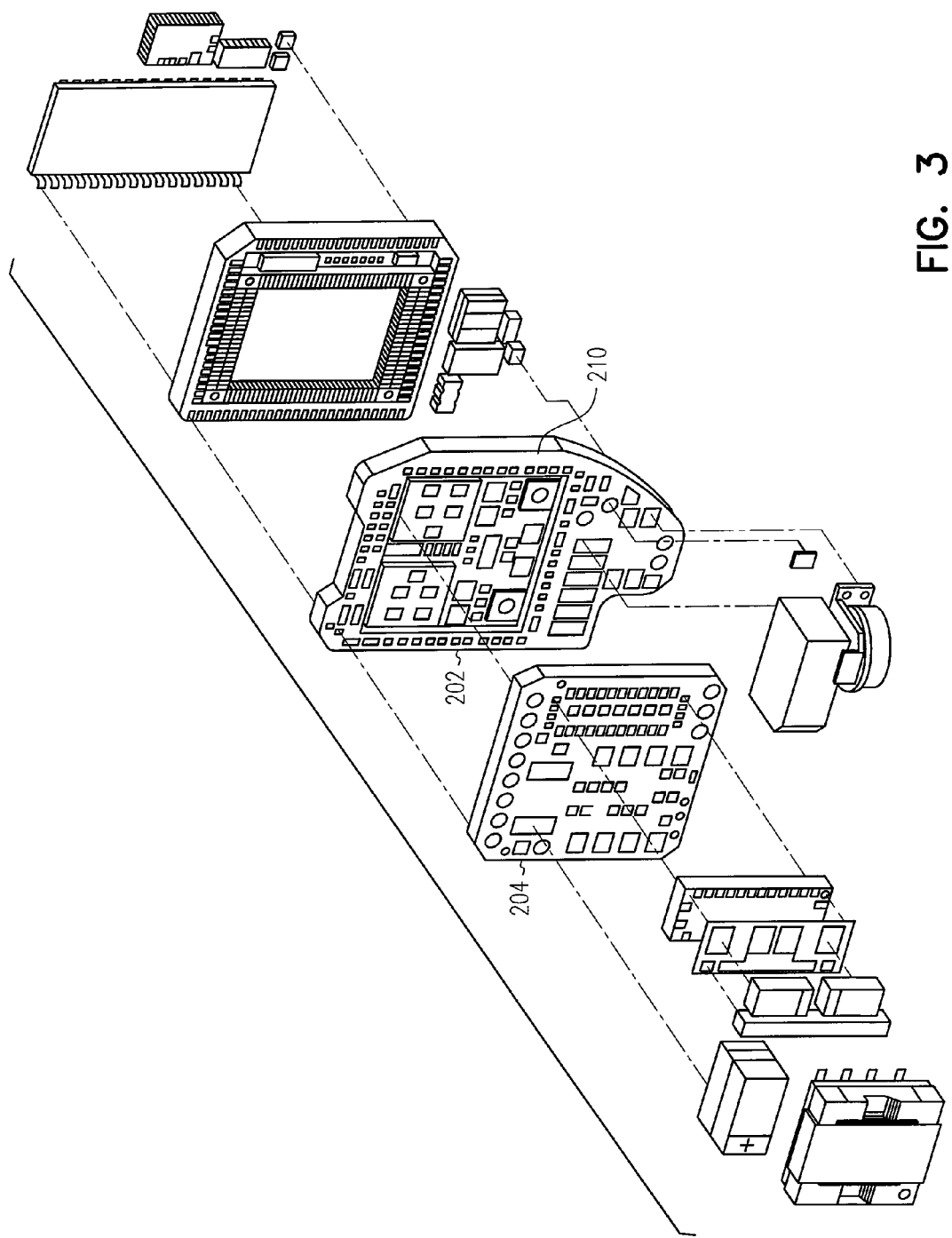
FIG. 3 is an exploded perspective view illustrating a substrate assembly constructed in accordance with another embodiment.
Figure 4A:
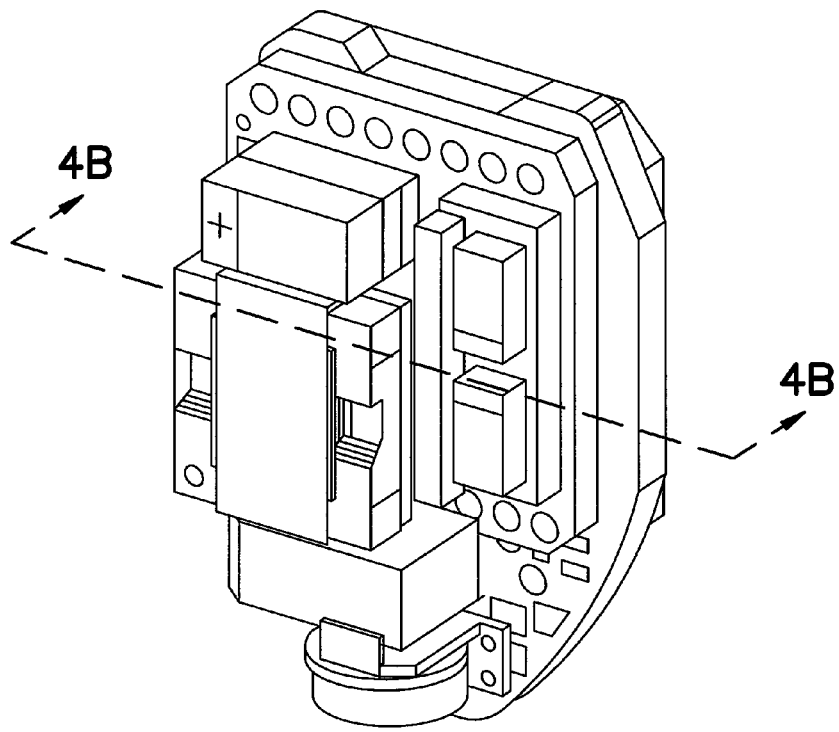
FIG. 4A is a perspective view illustrating an assembled substrate assembly constructed in accordance with one embodiment.
Figure 4B:
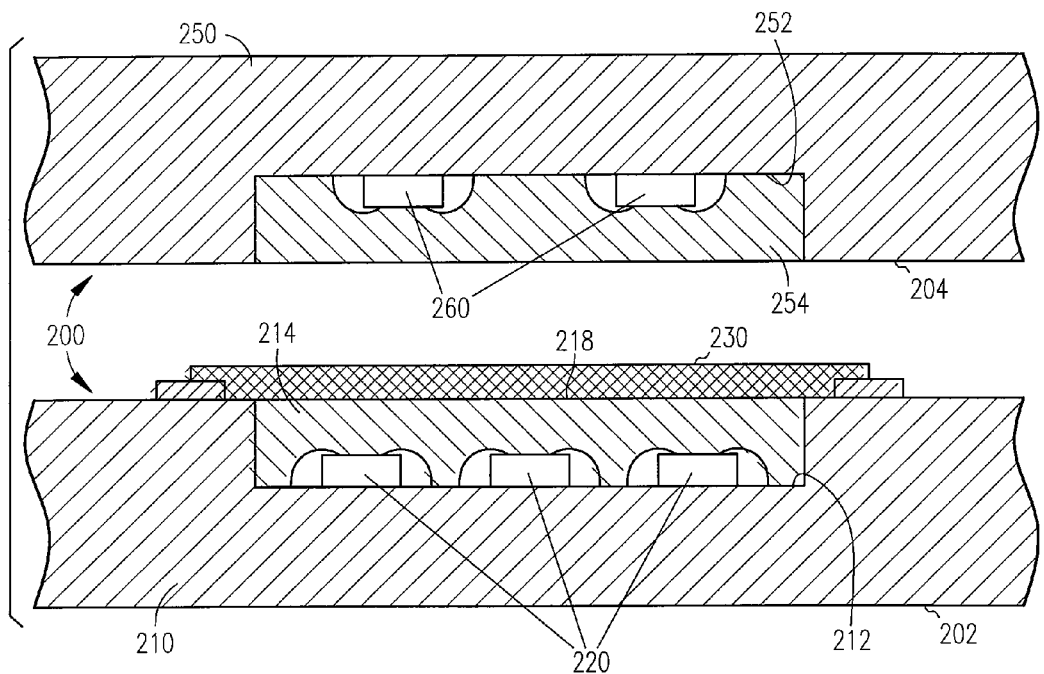
FIG. 4B is an exploded cross-sectional view of FIG. 4A taken along 4B-4B.

FIGS. 3, 4A and 4B illustrate another embodiment, and shows a substrate assembly 200 including a first substrate assembly 202 and a second substrate assembly 204. The first substrate assembly 202 includes a first substrate 210 having multiple components 220 disposed thereon. The multiple components 220, include, but are not limited to, at least one integrated circuit. The first substrate 210 has a cavity 212 therein, and the components 220 are populated on the substrate 210 within the cavity 212. The cavity 212 is filled with a dielectric polymer 214, where the polymer 214 is disposed over the components 220 to cover and insulate the components 220. In addition, the polymer 214 protects the components 220. One example of a suitable polymer is an epoxy. Other suitable materials include those which fill the voids or spaces amongst the components and which solidifies or becomes substantially rigid when cooled. The material should also have adequate compressive strength, and should also be lightweight. After the polymer 214 is disposed within the cavity 212, the polymer is cured at about 150 degrees C. to form a rigid to semi-rigid structure.

The polymer filling 214 is defined in part by an outer surface 218. A thin film metal is vapor deposited on the outer surface 218 of the polymer 214 to form a thin film 230, as shown in FIG. 4B. Alternatively, the thin film metal is vacuum deposited on the outer surface 218. To deposit the thin film metal, the atoms or molecules from a vaporization source reach the outer surface 218 of the polymer 214 without colliding with residual gas molecules. The vaporization source comprises one that thermally vaporizes materials, for example by evaporation or sublimation. Vacuum evaporation allows for a deposit of thin film of a variety of materials which can be deposited at high rates over large areas in a very pure form.

The thin film 230 at least partially covers the outer surface 218, and optionally covers the entire outer surface 218 of the polymer 214. Alternatively, the thin film metal is sputtered on to the outer surface 218 to form the thin film 230. It should be noted that the thin film 230 can be formed on the outer surface 218 prior to the polymer 214 being fully cured, or can be formed on the outer surface 218 after the polymer 214 is fully cured. The thin film is formed from a variety of conductive materials including, but not limited to, gold, aluminum, or copper. In one embodiment, the thin film 230 is formed to a thickness of about 25 microns. Optionally, the thin film 230 is electrically coupled with an electrical contact 232, as shown in FIG. 4B, such that the thin film 230 can be used for electrical isolation, and/or the thin film 230 forms a shield against EMI. Optionally, the electrical contact 232 is electrically coupled with a ground pin. Connecting the thin film 232 with ground electrically isolates the first substrate assembly 202 from the second substrate assembly 204.

The first substrate assembly 202 is coupled with the second substrate assembly 204, as shown in FIG. 4A, such that the first substrate assembly 202 is electrically isolated from the second substrate assembly 204. The second substrate assembly 204 includes a second substrate 250 having multiple components 260 disposed thereon. The multiple components 260, include, but are not limited to, at least one integrated circuit. The second substrate 250 has a cavity 252 therein, and the components 260 are populated on the second substrate 250 within the cavity 252. The cavity 252 is filled with a dielectric polymer 254, where the polymer 254 is disposed over the components 260 to cover and insulate the components 260. The polymer 254 is disposed on and/or within the second substrate 250 as discussed above for the first substrate assembly 202.

Figure 5:
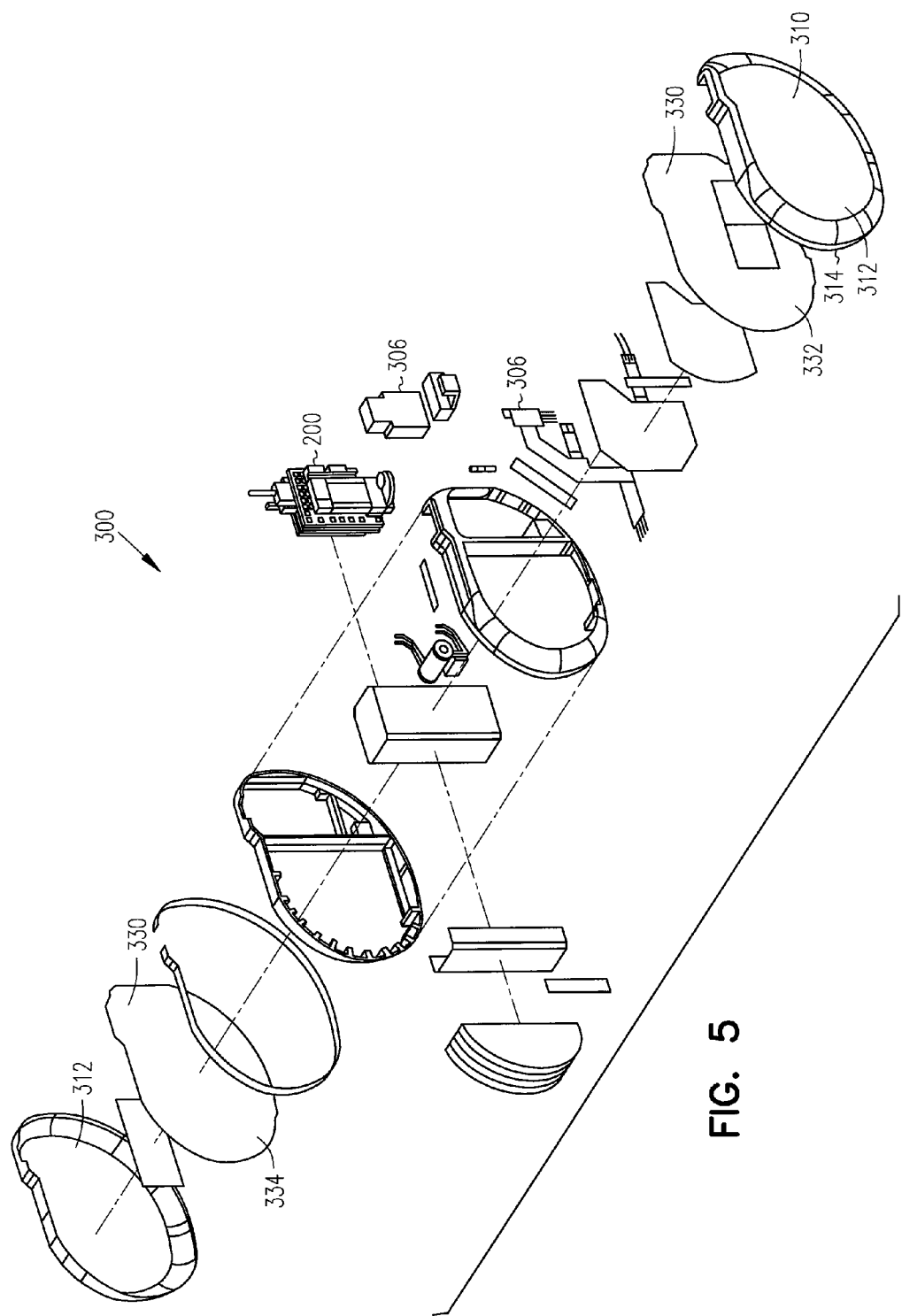
FIG. 5 is an exploded perspective view illustrating an implantable medical device constructed in accordance with another embodiment.

FIG. 5 illustrates an exploded medical device 300, such as an implantable pulse generator. The medical device 300 has a clamshell type case 310 having a pair of confronting concave halves 312 which, when mated, define a perimeter parting line 314. The confronting concave halves 312 are formed from a number of electrically conductive materials such as titanium, stainless steel or other bio-compatible material. The parting line 314 is sealed, for example by laser welding, to completely seal the electronic components within the enclosure or case.

The case 310 hermetically seals electronics, discussed further below, within the case in an airtight environment. Since the case 310 is sealed, the electronics are not damaged by contact with body fluids when the device is used subcutaneously in an individual. The case 310 also assists in providing structural integrity for the device to protect the electrical components held within the case 310. The case 310 must not deform or collapse when subjected to external compression forces during manufacture of the device, during an implant procedure, and once implanted within an individual.

Disposed within the case 310 are electronics including electronic components 306 and also the substrate assembly 200 including a first substrate assembly 202 and a second substrate assembly 204. The first substrate assembly 202 is coupled with the second substrate assembly 204 (FIG. 4A).

Optionally, the first substrate assembly 202 is coupled with the second substrate assembly 204, such that the first substrate assembly 202 is electrically isolated from the second substrate assembly 204. The second substrate assembly 204 includes a second substrate 250 having multiple components 260 disposed thereon, as discussed above.

The first substrate assembly 202 includes a first substrate 210 having multiple components 220 disposed thereon, as discussed above. The first substrate 210 includes the polymer filling 214, which is defined in part by an outer surface 218 (FIG. 4B). Optionally, a thin film metal is vapor deposited on the outer surface 218 of the polymer 214 to form a thin film 230, as shown in FIG. 4B. The thin film 230 at least partially covers the outer surface 218, and optionally covers the entire outer surface 218 of the polymer 214. Alternatively, the thin film metal is sputtered on to the outer surface 218 to form the thin film 230. The thin film is formed from a variety of conductive materials including, but not limited to, gold, aluminum, or copper.

The thin film 230 is electrically coupled with an electrical contact 232, as shown in FIG. 4B, such that the thin film 232 can be used for electrical isolation. Optionally, the electrical contact 232 is electrically coupled with a ground pin. Connecting the thin film 232 with ground electrically isolates the first substrate assembly 202 from the second substrate assembly 204.

Referring again to FIG. 5, at least one insulator 330 is disposed within the case 310. The insulator 330 is formed of a non-conductive material, for instance, a non-conductive polymer. The insulator 330 is disposed between one of the electrically conductive clamshell halves 312 and the substrate assembly 200. Optionally, an insulator 330 is disposed additionally or alternatively between one of the clamshell halves 312 and the electronic components 306. The insulator 330 is defined in part by a first surface 332 which is disposed proximate to one of the clamshell halves 312, and a second surface 334 which is disposed proximate to the second substrate assembly 200 or the electronic components 306.

Figure 6:
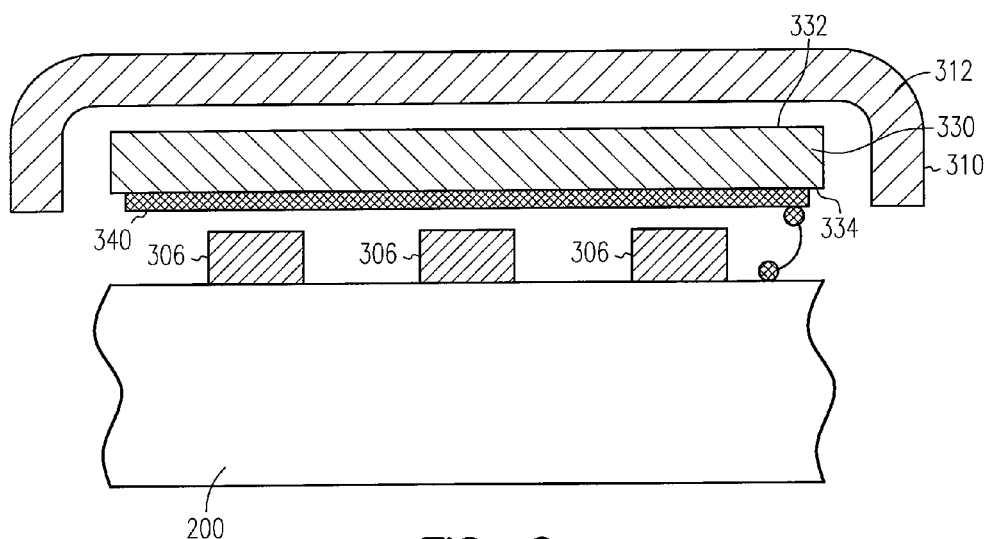
FIG. 6 is a cross-sectional view illustrating an implantable medical device constructed in accordance with an embodiment.

A thin film metal is vapor deposited on at least a portion of the second surface 334 of the insulator 330, as shown in greater detail in FIG. 6 to form a layer of thin film 340. To deposit the thin film metal, the atoms or molecules from a vaporization source reach the second surface 334 of the insulator 330 without colliding with residual gas molecules. The vaporization source comprises one that thermally vaporizes materials, for example by evaporation or sublimation. Vacuum evaporation allows for a deposit of thin film of a variety of materials which can be deposited at high rates over large areas in a very pure form. The thin film 340 at least partially covers the second surface 334, and optionally covers the entire second surface 334 of the insulator 330.

Alternatively, the thin film metal is sputtered on to the second surface 334 to form a thin film 340. In one embodiment, the thin film 340 is formed to a thickness of about 1 micron. Alternatively, the thin film 340 is formed to a thickness of up to about 25 microns. In contrast to the vapor deposition process which depends on heat to vaporize the material, sputtering is an atom-by-atom process. A target is bombarded by ions which physically chip atoms off of the target, causing them to be ejected from the target and subsequently strike the second surface 334 and adhere thereto. The atoms build up on the second surface 334 to form a layer of material, resulting in the thin film. The thin film is formed from a variety of conductive materials including, but not limited to, gold, aluminum, or copper.

It should be noted that the thin film 340 can be formed on the second surface 334 of the insulator 330 to form trace lines such that it can be used for electrical routing connections. For example, in forming the thin film 340, a part of the second surface 334 is masked off, such as with photoresist. Photoresist is a photosensitive coating that is applied to a laminate and subsequently exposed through a film. The photoresist is developed resulting in a pattern that can be either plated or etched with the thin film 340. The etched or plated thin film 340 forms trace lines, where the trace lines can be used for electrical connections, for example, between components. Alternatively, the thin film 340 is electrically connected with the substrate assembly 200, such that the thin film 340 is electrically coupled with a ground pin and the thin film 340 electrically isolates the substrate assembly 200 from the conductive case 310.

Figure 7:
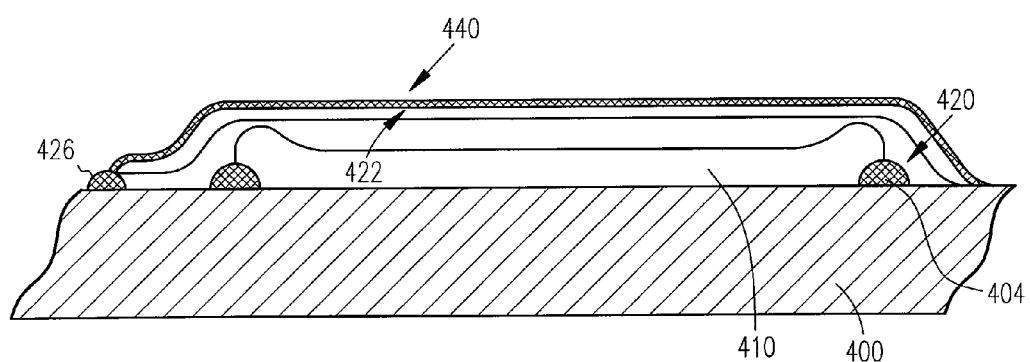
FIG. 7 is a cross-sectional view illustrating an implantable medical device constructed in accordance with an embodiment.

FIG. 7 illustrates another embodiment, including a substrate 400 having an electronic component 404. For instance, a resistor 410 is printed on the substrate and fired. Disposed over the resistor 410 is an insulator 420. Optionally, an overglaze 422 of insulating material is disposed over the insulator 420. A thin film metal is vapor deposited on at least a portion of the insulator 420, to form a layer of thin film 440. To deposit the thin film metal, the atoms or molecules from a vaporization source reach the insulator 420 without colliding with residual gas molecules. The vaporization source comprises one that thermally vaporizes materials, for example by evaporation or sublimation. Vacuum evaporation allows for a deposit of thin film of a variety of materials which can be deposited at high rates over large areas in a very pure form. The thin film 440 at least partially covers the insulator 420, and optionally covers the entire insulator 420. Alternatively, the thin film metal is sputtered on to the insulator to form a thin film 440. In one embodiment, the thin film 440 is formed to a thickness of about 1 micron. Alternatively, the thin film 440 is formed to a thickness of up to about 25 microns. The thin film is formed from a variety of conductive materials including, but not limited to, gold, aluminum, or copper. The thin film 440 is electrically coupled with an electrical contact 426, such that the electronic component 404 can be electrically isolated from surrounding components.

Advantageously, the above described method and apparatus does not use or require any heat generation to deposit the thin film and/or conductive interconnects. In addition, the method can be used on a wide variety of materials while maintaining adequate adhesion and conduction sufficient for use in an implantable medical device such as a defibrillator or pacemaker. Further, the surface on which the traces are deposited is not limited in geometry or topography. Since the thin film does not require high temperature during the deposition or sputtering process, the components which populate the substrate will not be harmed by high temperatures. In addition, since the thin film layer can be deposited very thin, the size of the medical device is not unnecessarily increased. Significant size reductions, material savings and substantial weight savings may be achieved utilizing the implantable medical device of the invention.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. An apparatus comprising:
  a medical device including an electrically conductive case;
  a first substrate assembly located within the medical device, the first substrate assembly including a first substrate having a cavity therein, a first set of electronic components disposed within the cavity, a first polymer disposed over the first set of components, the first polymer having an outer surface, a thin film of metal deposited on the outer surface, the thin film of metal electrically coupled with a ground; and
  a second substrate assembly including a second substrate, the second substrate having a second cavity with the electronic components disposed therein, the second substrate assembly being coupled with the first substrate assembly with the first cavity facing the second cavity, and wherein the film of metal deposited on the outer surface of the first polymer is located between the first substrate and the second substrate.

2. The apparatus as recited in claim 1, wherein the outer surface of the first polymer is non-planar.

3. The apparatus of claim 1, wherein the outer surface of the first polymer is planar.

4. The apparatus as recited in claim 1, further comprising an insulator disposed within the electrically conductive case adjacent an inner wall of the electrically conductive case.

5. The apparatus of claim 4, further comprising a thin film of metal deposited on at least a portion of the insulator.

6. An apparatus comprising:
  a medical device including an electrically conductive case;
  an insulator disposed within the electrically conductive case adjacent an inner wall of the electrically conductive case, the insulator having a film of metal deposited on at least a portion of the insulator; and
  a first substrate assembly located within the medical device, a first set of electronic components disposed a first cavity of the first substrate assembly, a first polymer disposed over the first set of components, the first polymer having an outer surface, and a film of metal deposited on the outer surface of the first polymer; and
  a second substrate assembly including a second substrate, the second substrate having a second cavity with the electronic components disposed therein, the second substrate assembly being coupled with the first substrate assembly with the first cavity facing the second cavity, and wherein the film of metal deposited on the outer surface of the first polymer is located between the first substrate and the second substrate.

7. The apparatus of claim 6, wherein the first substrate assembly including a cavity, with the first set of electronic components disposed within the cavity.

8. The apparatus of claim 6, further comprising a second substrate assembly including a second substrate, the second substrate having electronic components disposed thereon, the second substrate assembly being coupled with the first substrate assembly.

9. The apparatus of claim 8, wherein the film of metal deposited on the outer surface of the first polymer is located between the first substrate and the second substrate.

10. The apparatus of claim 6, wherein the film of metal deposited on the outer surface of the first polymer is coupled to an electrical ground.

11. The apparatus of claim 6, wherein the film of metal deposited on the outer surface of the first polymer is gold, copper, or aluminum.

12. The apparatus of claim 6, wherein a surface of the first polymer is non-planar.

13. The apparatus of claim 6, wherein the film of metal deposited on the outer surface of the first polymer has a thickness of up to about 25 microns.

14. An apparatus comprising:
  a medical device including an electrically conductive case;

a first substrate located within the electrically conductive case, the first substrate having a first set of electronic components disposed within a first cavity of the first substrate, a first polymer disposed over the first set of components, the first polymer having an outer surface, a thin film of metal located on the outer surface, the thin film of metal electrically coupled with a ground; and a second substrate assembly including a second substrate, the second substrate having electronic components disposed within a second cavity of the second substrate, the second substrate assembly being coupled with the first substrate assembly with the first cavity facing the second cavity and such that the thin film of metal is between the electronic components on the first substrate and the electronic components on the second substrate.

15. The apparatus as recited in claim 14, wherein the outer surface of the first polymer is non-planar.

16. The apparatus as recited in claim 14, wherein the electrically conductive case includes an insulator disposed therein and a thin film of metal is vapor deposited on at least a portion of the insulator.

* * * * *